United States Patent [19]

Blase et al.

[11] Patent Number: 5,576,024
[45] Date of Patent: Nov. 19, 1996

[54] BUFFERED MATRIX ASPIRIN

[76] Inventors: Cynthia M. Blase, English Village Apts., #21, C-2, North Wales, Pa. 19454; Garnet E. Peck, 808 Cumberland Ave., West Lafayette, India. 47906

[21] Appl. No.: 465,381

[22] Filed: Jun. 5, 1995

Related U.S. Application Data

[63] Continuation of Ser. No. 927,880, Aug. 10, 1992, abandoned, which is a continuation of Ser. No. 702,504, May 20, 1991, abandoned.

[51] Int. Cl.⁶ ..................................................... A61K 9/36
[52] U.S. Cl. .......................... 424/488; 424/480; 424/482; 424/484; 424/486; 424/494; 424/497
[58] Field of Search .................................... 424/480, 482, 424/484, 494, 497, 486, 488

[56] References Cited

U.S. PATENT DOCUMENTS

| | | | |
|---|---|---|---|
| 3,341,416 | 9/1967 | Anderson et al. | 424/497 |
| 3,946,110 | 3/1976 | Hill | 424/230 |
| 4,153,677 | 5/1979 | John | 424/19 |
| 4,369,172 | 1/1983 | Schor et al. | 424/19 |
| 4,555,399 | 11/1985 | Hsiao | 424/35 |
| 4,869,984 | 9/1989 | Patel | 424/458 |
| 4,970,081 | 11/1990 | Frisbee | 424/480 |

FOREIGN PATENT DOCUMENTS 0207041  12/1986  European Pat. Off. .

OTHER PUBLICATIONS

Van Nostrand Reinhold Encyclopedia of Chemistry 4th edition, pp. 149–150 (1984).

*Primary Examiner*—Jyothsna Venkat
*Attorney, Agent, or Firm*—M. G. Boguslaski

[57] ABSTRACT

A buffered aspirin tablet composed of a uniform mixture of aqueous-based polymer coated aspirin, a buffering system and a hydrophillic gel-forming matrix material. The buffering system and matrix material provide a microenvironment on in vitro dissolution of about pH 5. The tablet does not require the use of multilayers and may be prepared by direct compression with conventional equipment.

8 Claims, No Drawings

BUFFERED MATRIX ASPIRIN

This is a continuation, of application Ser. No. 07/927,880, filed Aug. 10, 1992, now abandoned, which is a continuation of U.S. Ser. No. 702,504 filed May 20, 1991 now abandoned.

FIELD OF THE INVENTION

The invention relates to buffered aspirin tablets in general and to polymer coated aspirin crystals which may be formulated in a uniform mixture with a buffer and a gel-forming matrix material.

BACKGROUND OF THE INVENTION

Aspirin is used widely as an analgesic, antipyretic, and antirheumatic agent. The major disadvantage of aspirin therapy is gastrointestinal irritation caused by direct contact of the solid aspirin crystals and the gastric mucosa which causes gastrointestinal bleeding. Buffered aspirin tablets have been developed to reduce gastrointestinal bleeding. However, these multilayer tablets have proven to be, at times, ineffective.

SUMMARY OF THE INVENTION

A composition comprising a uniform mixture of aqueous-based polymer coated aspirin crystals, a buffering system and a hydrophillic gel-forming matrix material to provide a microenvironment around the coated aspirin crystals of about pH 5 to aid in increasing aspirin solubility. A preferred tablet formulation contains aspirin crystals coated with 3 to 6 % by weight aqueous-based polymer chosen from the group consisting of polyvinylpyrrolidone or hydroxypropylmethylcellulose; at least 25% by weight of calcium carbonate buffer; and from about 5 to less than 15% by weight of a hydroxypropylmethylcellulose capable of providing a low viscosity solution when dissolved in an aqueous solution. The formulation may be mixed to provide a uniform mixture and tableted by direct compression with conventional equipment.

DESCRIPTION OF THE INVENTION

Some researchers have postulated that the inefficacy of buffered aspirin tablets may be due to cohesion problems with the multilayered tablets. Upon tablet ingestion, the layers may laminate at their interface so that the aspirin and buffer are no longer in close proximity. Therefore the amount of buffer around the aspirin is insufficient to affect the gastric fluid pH and therefore is ineffective in increasing aspirin solubility.

The objective of this invention was to produce a unique buffered aspirin tablet, in which the aspirin and buffer were uniformly mixed throughout the entire tablet matrix. This objective was achieved by coating aspirin crystals with an aqueous-based polymeric coating system using a Glatt GPCG5 fluid bed. The coating served as a protective barrier against aspirin and tablet component incompatibilities.

The coated aspirin crystals were incorporated into a tablet matrix which was evaluated using dissolution, micro-pH, and stability studies. The goals for the system were:

1. To achieve tablet erosion rather than tablet disintegration into individual particles using a gel-forming matrix material to maintain the tablet intact until completely eroded.

2. To create a microenvironment of increased pH within and around the tablet as gastric fluid penetrates the tablet matrix due to buffer dissolution, which aids in increasing aspirin solubility.

3. To produce a tablet exhibiting a fast aspirin release rate and acceptable stability.

4. To produce an economical system by formulating a directly compressed tablet using conventional tablet and aqueous film coating technology and equipment.

The buffered aspirin tablet composition comprises a uniform mixture of aqueous-based polymer coated aspirin crystals, a buffering system and a hydrophillic gel-forming matrix material to a microenvironment on dissolution of about pH 5. Additionally the composition may contain a binder and a hydrophobic lubricant as well as other excipients to facilitate tabletting or stability.

The aqueous-based polymer coating should provide sufficient protection for the aspirin crystals to prevent reaction with the other tablet components prior to dissolution. It has been found that useful polymers include, but are not limited to, polyvinylpyrrolidone (PVP such as Plasdone K29-32, GAF Corp., New York, N.Y.), hydroxypropylmethylcellulose (HPMC such as HPMC E15LV, HPMC E5, and HPMC E3 Premium which may be obtained from Dow Chemical Co., Midland, Mich.), methylcellulose (MC such as MC A15LV which may be obtained from Dow Chemical Co., Midland, Mich.), sodium carboxymethylcellulose (NaCMC, such as NaCMC 7LF and NaCMC 7MF which may be obtained from Hercules Inc., Wilmington, Del.), microcrystalline cellulose, having a particle size of between about 20 and 100 μm, (MCC, such as Avicel PH 101, Avicel PH 103, Avicel RC591 and Avicel CL661 which may be obtained from FMC Corp., Philadelphia, Pa.) and hydroxypropylcellulose (HPC such as Klucel EF and Klucel LF which may be obtained from Hercules Inc., Wilmington, Del).

The hydrophillic gel-forming matrix may be prepared with gel-forming matrix materials which are often used for controlled release formulations, such as the HPMC K series polymers manufactured by The Dow Chemical Company, Midland, Mich. 48674. Since it is an object of this invention to obtain rapid disintegration and release of the aspirin, low viscosity members of the series, such as HPMC K100LV, are preferred and should be used in a concentration of less than about 15 percent by weight of the tablet formulation.

The buffering system is one which, in conjunction with the gel-forming matrix material provides a microenvironment of about pH 5 on in vitro dissolution of the tablet. A preferred buffer is calcium carbonate in a concentration of at least 25% of the tablet weight. The use of this buffer has the added advantage of avoiding the addition of large amounts of sodium and providing a calcium supplement.

Direct compression formulation of tablets usually requires the addition of excipients in order to obtain the desired tablet properties such as mechanical strength and disintegration and of lubricants to facilitate the ejection of the tablet from the die during the tabletting process. Such components are well known to those of skill in the art and should be chosen to avoid incompatibilities with the components of the buffered aspirin system, especially with the aspirin. Two particularly preferred components due to their affect on an aspirin formulation are microcrystalline cellulose as the excipient and stearic acid as the lubricant. The excipient acts in a multitude of functions including a binder, disintegrant, flow promoter and/or diluent. Useful microcrystalline celluloses include those with a particle size range of about 25 to about 150 micrometers, preferably from about 25 to 75 micrometers, most preferably about 50 micrometers. Hydrophobic lubricants are preferred. Special care should be taken to avoid incompatibilities of the lubricant with aspirin. Useful lubricants include vegetable stearin and talc as well as others readily available to those of skill in the art.

The formulation may be prepared by coating aspirin crystals with an aqueous based polymer, preferably with fluidized bed coating equipment, mixing the coated aspirin crystals with a buffer, a gel-forming matrix material, and other components as desired to facilitate tabletting to produce a uniform mixture; and tablets may then be manufactured by direct compression with conventional equipment. Aspirin crystals useful for coating should be between 20 and 200 mesh; most preferred is a particle size of between 20 and up to about 50 mesh.

The following examples disclose preferred embodiments of the invention, but do not limit the applicability of the invention which is solely defined by the claims.

EXAMPLES

Preparation of the dosage form was restricted to conventional tabletting and aqueous film coating technology and equipment. All materials were FDA approved and the use of organic solvents was avoided. All percentages given are weight/weight unless otherwise indicated.

Example 1—Coating of Aspirin Crystals

Preparation of Aqueous-Based Polymeric Coating Solutions

The quantity of each ingredient was measured by weight. Weighing was performed on an Ohaus two-pan balance. (Ohaus Dial-0-Gram Balance, Series 200 2 kg capacity, Ohaus, Florham Park, N.J.) The polymer was slowly dispersed in the distilled water. Agitation was provided by a marine propeller mixer. (Lightnin' Mixer, Mixing Equipment Co., Rochester, N.Y.) For the cellulosic polymers that required dispersion in hot water, the distilled water was heated on a hot plate to 30° C. prior to addition of the polymer. The coating solutions were stored in a refrigerator until use and discarded if not used 48 hours after preparation. Additives, such as plasticizers and colorants, were added after adequate polymer dispersion and mixed well. A plasticizer was added to some of the cellulosic polymeric coating solutions to produce a more pliable, stronger film that could resist mechanical stress. The most effective plasticizers closely resemble in structure the polymers they plasticize. The polymers which required a plasticizer were the cellulose ethers which contain a large portion of hydroxyl groups. Therefore they are best plasticized with hydroxyl-containing materials such as polyols, glycerol, propylene glycol, and polyethylene glycols of molecular weight 200–8000. A colorant was incorporated into the coating solutions as a visual aid. In aqueous film coating, use is made of aluminum lakes of water-soluble dyes. In this study, Aluminum FD&C Red #3 was used in a concentration of 0–01%. A typical aqueous-based polymeric coating solution used in this study is shown in Table 1.

TABLE 1

A Typical Formula for an Aqueous-Based Polymeric Coating Solution

| Ingredient | Percent |
| --- | --- |
| Hydroxypropylmethylcellulose (HPMC E5) | 6.0 |
| Propylene Glycol | 1.0 |
| FD&C Red #3 | 0.01 |
| Distilled Water | q.s to 100 |

A standard coating pan and an air suspension six inch column were used to screen potential polymers with aspirin crystals of 100 to 200 mesh. Later work indicated that aspirin crystals of from 20 to 200 mesh may be coated successfully. (Propylene Glycol was obtained from Ruger Chemical Co., Irvington, N.J.; FD&C Red #3 was obtained from Warner Jenkinson, St. Louis, Mo..) After screening, Glatt GPCG5 coating was used as the preferred method to coat the aspirin crystals.

Glatt GPCG5 Coating of Aspirin Crystals

Aspirin crystals were successfully coated using top-spray, bottom-spray and tangential-spray fluid bed coating processes. Preferred equipment for coating is a Glatt GPCG5 Fluid Bed equipped with a top-spray apparatus (Glatt GPCG5 Fluid Bed with Top-Spray Apparatus, Glatt). In a preferred procedure, a 5 kilogram aspirin crystal load was placed in the product container. The crystals were fluidized in an expansion chamber. The spray nozzle was located low in the expansion chamber so that liquid was applied when the crystals were moving at a higher velocity. This served to minimize surface wetting and to inhibit agglomeration. A filter was used to separate entrained crystals from the exiting process air stream. The pump was calibrated with coating solution prior to start up of the coating process. The turbine was activated and the process air was heated to 55° C. The spray and shake cycle was started and ran continually until the coating solution was completely depleted. The coated aspirin crystal bed was dried for 10 minutes and the product was cooled to 35° C. The product was removed, weighed and passed through a 20 mesh screen to remove any agglomerates.

Coatings prepared as discussed above can also be applied with a UniGlatt with a 6 inch Wurster insert (Uniglatt Laboratory 6" Coating Column, Glatt, 7859 Holtengen/ Brinzen, Germany) and a Standard Coating pan (Colton Standard Pan Coater, Vector Corp., Marion, Iowa).

Example 2 Preferred Formulations

Tablets were prepared containing five components: 50% by weight aspirin crystals (100–200 mesh) coated previously with 3 to 6% polyvinylpyrrolidone; 25% calcium carbonate buffer, 5 to 15% hydroxypropymethyl cellulose (K100LV) as the gel forming hydrophillic matrix material; 14.5 to 19.5% microcrystalline cellulose (Avicel PH 101) as the excipient/binder; and 0.5% stearic acid as the hydrophobic lubricant. All materials were used as supplied.

The components of the tablet formulation were weighed and mixed. Six hundred fifty milligram (mg) samples were compressed on a Carver Laboratory Press (from Fred S. Carver, Cin., Summit, N.J.) using ½ inch punches and dies at a compression pressure of 5000 pounds (lbs). The standard U.S.P. dissolution Method II was used to evaluate the aspirin release from the buffered matrix tablets. The dissolution media was 900 milliliters (mL) of 37° C., pH 1.2 simulated gastric fluid. Triplicate samples were withdrawn at appropriate time intervals and analyzed for aspirin and salicylic acid content using High Performance Liquid Chromatography (HPLC).

The formulation was scaled-up and run on a sixteen station Stokes B-2 tablet press (Stokes B Tablet RB2 Machine, F. J. Stokes Machine Co., Philadelphia, Pa.). Tablet hardness and friability were evaluated by standard procedures. The tablets were subjected to dissolution testing using the U.S.P. Method II, the paddle method. Testing was also done to evaluate the hypothesis that a microenvironment of increased pH was created within and around the buffered matrix tablet due to the buffer and the gel-forming matrix material that maintained the tablet intact until completely eroded.

Testing showed that as the coating level increased, the tablet dissolution rate decreased. The higher levels of PVP coated aspirin crystals (3 to 6%) had statistically significantly slower aspirin release rates than the crystals coated with 0 to 2% PVP. Upon visual observation, it was noted that the tablets eroded rather than disintegrated into individual particles. In addition it was shown that the use of a polymer coating can reduce the formation of the degradation product, salicylic acid providing improved aspirin stability.

Aspirin release profiles for various buffer system levels indicate that to produce a preferred rapid aspirin release rate from the eroding tablet matrix, at least about 25% of a calcium carbonate buffer is required. The release rate was not significantly different with up to about 40% calcium carbonate buffer. However, the lower level is most preferred because at the high buffer levels, the tablet formulation could not be altered to any great extent.

TABLE 2

The Physical Properties of the Tablet Formulations Produced in the Scale-Up Study

| Formulation* ASA Type HPMC K100LV Level | Weight Variation (mg)** | Hardness (kp) | Dissolution Rate (% ASA/30 min) |
| --- | --- | --- | --- |
| Uncoated ASA 5% HPMC K100LV | 653.8 | 8.4 | 99.2 |
| 3% Coated ASA 5% HPMC K100LV | 652.5 | 9.0 | 99.9 |
| 6% Coated ASA 5% HPMC K100LV | 651.5 | 9.4 | 92.2 |
| 3% Coated ASA 10% HPMC K100LV | 654.2 | 9.8 | 96.0 |

*Formulations also contained 25% buffer system, Avicel PH 101, and 0.5% stearic acid.
**The standard error ranged between 2.5 mg and 5.7 mg.

Table 2 lists formulations and physical properties of experimental tablets which were scaled-up to two kilogram (kg) pilot lots on a Stokes B-2 16 station tablet press. Friability for these experiments was out of the acceptable range but may be improved by either increasing tablet hardness or by adding other excipients. The weight variation for all of the batches produced was minimal. Tablet hardness and dissolution were well within the acceptable ranges. Greater than 90 percent aspirin was released for all of the formulations indicating good content uniformity of the tablets due to proper mixing and flow of the direct compression formulation on the tablet press. A micro-pH study was conducted to confirm the existence of a microenvironment of increased pH within and around the tablet matrix due to the buffer system and tablet erosion. The aspirin and the buffer remained in close proximity during tablet erosion.

The buffer solubilized as the simulated gastric fluid penetrated the tablet core thereby producing a higher pH within and around the tablet matrix. The increased pH allowed for increased aspirin solubility versus the low pH of the simulated gastric fluid. The micro pH profiles showed that the pH within and around the tablet matrix was maintained at approximately pH 5 for the entire tablet erosion process. After the tablets were completely eroded the pH dramatically dropped to pH 1.2 since the tablet was no longer present. The bulk pH of the dissolution medium was also monitored. The simulated gastric fluid pH varied only one or two tenths of a pH unit, indicating that the buffer did not change the pH of the entire 900 mL dissolution medium.

An increase in the concentration of hydroxypropylmethylcellulose (HPMC K100LV) in the matrix system increases the viscosity of the gel that forms on the tablet surface during dissolution. Therefore, an increase in the level of HPMC K100LV will yield a decrease in the aspirin release from the buffered matrix tablet. This behavior was observed in simulated gastric fluid for tablets produced with from about 5 to about 25% HPMC K100LV. Preferred formulations containing from about 5 to about 12.5% HPMC K100LV provided the desired fast aspirin release rate. Gel-forming matrix material levels of from about 13.75% to about 25% of the total tablet weight provided tablets with prolonged release characteristics.

The buffer acts mainly at the tablet surface and within the gelatinous layer around the tablet matrix. At 25% buffer, the system maintained a pH of approximately 5 for 5 to 6 minutes, allowing the tablet to erode completely, after which the micro-pH dropped to the pH of the simulated gastric fluid. Fifteen (15%) percent buffer was insufficient to maintain the pH for a time sufficient for complete erosion with this tablet formulation. Similarly, for this tablet formulation, the micro-pH profile for 35% buffer was not constant. The pH gradually decreased with time, indicating that the higher level of buffer in this formulation caused a disruption of the tablet matrix due to the nature of the buffer system's disintegration mechanism. Substitutions for buffer showed that magnesium carbonate also maintained a constant micro-pH for the entire erosion process.

Micro-pH profiles for tablets produced with 5, 10 or 15 percent gel-forming matrix material showed that 5 and 10% levels exhibited very similar behavior. The micro-pH was maintained at pH 5 for the entire erosion process. The 15 percent level also maintained the micro-pH at 5. However, this level of gel former is less preferred because a more viscous gel layer is produced which causes a decrease in the tablet erosion time due to the increased time required for complete polymer hydration.

It should be understood that many modifications and variations can be made in the proportions and components used herein without departing from the spirit and scope of the invention, which is solely defined by the claims.

What is claimed is:

1. A uniform buffered aspirin tablet comprising a uniform mixture of:

a. aspirin crystals coated with from about 3 to about 6 percent by weight of an aqueous based polymer selected from the group consisting of polyvinylpyrrolidone and hydroxypropylmethylcellulose;

b. from about 25 to about 40% by weight of a buffer component capable of providing a microenvironment of about ph 5 around the coated aspirin crystals during dissolution, thereby, increasing the solubility of the aspirin, which buffer component is selected from the group consisting of calcium carbonate and magnesium carbonate; and c. an amount of a hydrophilic gel-forming matrix material in the weight range from about 5% to less than about 15% by weight, which gel-forming material is hydroxypropyl methylcellulose selected from the group consisting of polyvinylpyrrolidone and hydroxypropylmethylcellulose.

2. The tablet of claim 1 wherein the aspirin crystals have a particle size of 20 to 200 mesh.

3. The tablet of claim 1 which additionally contains a binder and a hydrophobic lubricant.

4. The tablet of claim 3 wherein the binder is a microcrystalline cellulose and the hydrophobic lubricant is stearic acid.

5. A uniform buffered aspirin tablet, comprising by weight:

a. about 50% aspirin crystals coated with from about 3 to about 6 percent by weight polyvinylpyrolidone;

b. from about 25 percent to about 40 percent by weight of calcium carbonate; and c. an amount of hydroxypropyl methylcellulose having methoxy content from 19–24% and hydroxypropoxy content from 4–12% in the weight range of a minimum of about 5 percent by weight to a maximum of 15 percent by weight.

6. The uniform buffered aspirin tablet of claim 4 wherein the aspirin crystals have a particle range of between 20 and 200 mesh and the microcrystalline cellulose has a particle range of between about 25 and 75 micrometers.

7. The tablet of claim 5, which additionally contains a binder.

8. The tablet of claim 7, wherein the binder is a microcrystalline cellulose.

* * * * *